US007370655B2

(12) United States Patent
Taylor (10) Patent No.: US 7,370,655 B2
(45) Date of Patent: May 13, 2008

(54) METHOD OF FORMING AN EARPLUG BY LASER ABLATION AND AN EARPLUG FORMED THEREBY

(75) Inventor: Duncan Taylor, Indianapolis, IN (US)

(73) Assignee: Cabot Safety Intermediate Corporation, Newark, DE (US)

( * ) Notice: Subject to any disclaimer, the term of this patent is extended or adjusted under 35 U.S.C. 154(b) by 729 days.

(21) Appl. No.: 10/346,604

(22) Filed: Jan. 17, 2003

(65) Prior Publication Data

US 2004/0139976 A1 Jul. 22, 2004

(51) Int. Cl.
  *A61F 11/00* (2006.01)
(52) U.S. Cl. ...................... 128/864; 181/135
(58) Field of Classification Search ........ 128/864–868; 181/135
  See application file for complete search history.

(56) References Cited

U.S. PATENT DOCUMENTS

| 4,915,981 | A | 4/1990 | Traskos et al. |
| 4,936,411 | A | 6/1990 | Leonard |
| 4,975,967 | A | 12/1990 | Rasmussen |
| 5,044,463 | A | 9/1991 | Carr |
| 5,573,015 | A | 11/1996 | Williams |
| 5,792,998 | A | 8/1998 | Gardner, Jr. et al. |
| 6,148,821 | A | * 11/2000 | Falco ............ 128/864 |
| 6,408,981 | B1 | 6/2002 | Smith et al. |
| 6,484,842 | B1 | 11/2002 | Widmer et al. |
| 6,492,616 | B1 | 12/2002 | Tanaka et al. |
| 6,533,062 | B1 | 3/2003 | Widmer et al. |
| 6,595,317 | B1 | 7/2003 | Widmer et al. |
| 6,766,878 | B2 | 7/2004 | Widmer et al. |
| 2001/0027965 | A1 | 10/2001 | McCay et al. |
| 2001/0047729 | A1 | 12/2001 | Maude et al. |
| 2002/0179365 | A1 | 12/2002 | Meussen et al. |
| 2003/0029460 | A1 | 2/2003 | Tiemens |
| 2003/0037989 | A1 | 2/2003 | Widmer et al. |
| 2003/0075185 | A1 | 4/2003 | Ulbrich |
| 2003/0133583 | A1 | 7/2003 | Widmer et al. |

FOREIGN PATENT DOCUMENTS

| EP | 1 046 382 | 10/2000 |
| WO | WO 98/25558 | 6/1998 |
| WO | WO 02/26465 | 4/2002 |
| WO | WO 03/013389 | 2/2003 |

* cited by examiner

*Primary Examiner*—Michael A. Brown
(74) *Attorney, Agent, or Firm*—Cantor Colburn LLP (57) ABSTRACT

A method of forming an earplug is provided including removing a material of the earplug by laser ablation. An earplug is positioned proximate a laser, a portion of the earplug to be ablated is identified, the laser is activated so as to direct an emitted laser light toward the portion to be ablated, and the portion to be ablated is removed by laser ablation. The invention is also directed to an earplug including a feature formed by laser ablation.

6 Claims, 8 Drawing Sheets

METHOD OF FORMING AN EARPLUG BY LASER ABLATION AND AN EARPLUG FORMED THEREBY

BACKGROUND OF INVENTION (a) Field of Invention

The invention relates generally to hearing protection devices and, more particularly to a method of forming an earplug by laser ablation.

(b) Description of Related Art

The use of hearing protective and noise attenuating devices is well known, and various types of devices are available including, but not limited to, ear muffs, semi-aural devices, and earplugs. Earplugs are often preferred for their effectiveness in attenuating sound and for comfort properties provided thereby.

An earplug generally comprises a sound attenuating element which is placed in the ear canal of a wearer to provide desired sound attenuation. The sound attenuating element is commonly made of a compressible, resilient material such as a foam or a rubber.

There are many instances in which it is desirable to produce the sound attenuating element having a cavity formed therein or a channel formed therethrough or, more generally, with a certain quantity of the compressible, resilient material removed or otherwise made absent from a body of the sound attenuating element.

For example, a cavity formed in the sound attenuating element of an earplug may be used to receive an end of a cord element which is bonded to the sound attenuating element in the cavity and used to connect two earplugs together. Herein, the term "cavity" will be used to designate a hole or recess formed in the sound attenuating element of an earplug but not completely through the sound attenuating element.

Such a cavity may be used in another embodiment to receive and mount therein a rigid or semi-rigid stem used to provide a degree of rigidity to the earplug and to effect convenient insertion and removal thereof. Still further, such a cavity may be formed in an earplug to receive a detectable material such as a metal, magnetic or x-ray identifiable substance for providing easy detectability of the earplug. Still further, a cavity may be formed within the sound attenuating element so that the earplug exerts less pressure on a wearer's ear canal upon insertion thereof, thus providing greater comfort to the wearer.

A channel formed through the sound attenuating element of an earplug may be used to facilitate communication with the wearer of the earplug. Herein, the term "channel" will be used to designate a hole or recess formed in a sound attenuating element of an earplug which propagates completely through the sound attenuating element such that the channel is open to an exterior of the earplug in at least two places.

Such a channel may be used to facilitate communication by, for example, receiving a communications insert, such as a receiver, transducer, etc., designed to deliver sound to a wearer. Alternatively, the channel may receive a tube for connection to a communication assembly which delivers sounds through the tube, into the ear canal of the wearer.

In another example, a certain quantity of the compressible, resilient material used to compose the sound attenuating element of an earplug may be desired to be removed or otherwise made absent from an outer surface of the element in order to form surface ornamentation, such as indicia or patterning, thereon. Such indicia includes characters and logos while the patterning includes surface elements for visual styling, gripping, etc.

The items discussed above (the cavity, channel, surface ornamentation) and other similar features may be formed in the earplug sound attenuating element either during production or shortly after production thereof.

For example, where the sound attenuating element is formed in a molding process, such as an injection molding process, the mold may include features which form the items, in situ, during molding. For example, the mold may include an insert about which the sound attenuating element is formed. Removal of the insert after formation of the compressible, resilient material results in the desired cavity or channel. The mold may include other elements which function similarly to the insert in order to form the surface ornamentation, i.e., indicia, patterning, etc.

However, such a molding technique often results in inconsistent formation of the described items. That is, it has been found that the sizing and placement of the cavity, the channel, etc. formed through in situ molding techniques often varies from one earplug to the next. Such inconsistent results are clearly not desirable. In addition, an earplug manufacturer would require several different earplug molds in order to produce sound attenuating elements having cavities, channels, and/or surface ornamentation, thus, increasing costs and generally complicating manufacturing.

The sound attenuating element of an earplug may also be formed through a casting process in which the resilient, compressible material, is formed in a sheet and then later die cut into pieces to form sound attenuating elements. Formation of the cavity, channel, or surface ornamentation during this casting process is not possible. Such features must be formed after casting of the sound attenuating elements by mechanical means, etc. However, this involves additional manufacturing and processing steps and, additionally, the features produced are often inconsistent from one attenuating element to the next or are otherwise inadequate.

Extrusion processes are often used to form the compressible, resilient sound attenuating elements for earplugs. However, such processes do not allow for creation of cavities or channels in the sound attenuating elements during formation thereof. Thus, in the case of extruded sound attenuating elements, as well as with preformed molded sound attenuating elements, features such as cavities, channels, or surface ornamentation must be formed in the sound attenuating element in a separate manufacturing step conducted after the initial formation of the sound attenuating element.

For example, after formation of a sound attenuating element, the cavity, channel, etc., may be effectively cut into the compressible, resilient material. Particularly, a high speed drill may be used to bore the cavity or channel into the sound attenuating element. However, this technique is insufficient because the drill tends to rip or tear the compressible, resilient material. Also, the rotating drill may pull the sound attenuating element from its fixture during drilling, thus interrupting manufacturing. In another technique, a thermal element having a high temperature is pressed into the sound attenuating element to effectively melt the compressible, resilient material in order to form the cavity, channel, etc. However, this method also results in inconsistent formation of the cavity, channel, etc. Specifically, a diameter of the cavity and channel varies considerably over manufacture of a number of earplugs, at least partly due to a build up of burnt compressible, resilient material adhering to the thermal element.

As mentioned, a sound attenuating element of an earplug may be formed to include a cavity for receiving a rigid or semi-rigid stem used to provide a degree of rigidity to the earplug and to effect convenient insertion and removal thereof. In one embodiment, the stem includes a stem cavity formed at one end of the stem for receiving an end of a cord element therein. The cord element is attached to the stem in the stem cavity and attached at an opposite end to a second stem of a second earplug, thus forming a corded pair of stemmed earplugs.

The stem may be formed, for example, by an extrusion process. During such process it is not possible to form the stem cavity. The stem cavity must be formed in a separate manufacturing process, for example, by boring a hole into the stem with a drill after extrusion formation of the stem. Alternatively, the stem may be produced through a molding or a casting process in which the stem cavity is created, respectively, in situ during formation of the stem or afterwards via a mechanical process. In either case, formation of the stem cavity by traditional methods often results in inconsistent placement of the cavity within the stem and inaccurate cavity dimensions.

Thus, a method of removing material from an earplug to effectively, efficiently, and consistently form surface elements in the earplug's sound attenuating element or stem, such as a cavity, a through-channel, and surface ornamentation, is desired.

SUMMARY OF INVENTION

The above discussed and other problems and deficiencies of the prior art are overcome or alleviated by the hearing protective device and method of manufacture of the invention.

A method of forming an earplug is provided including removing a material of the earplug by laser ablation. An earplug is positioned proximate a laser, a portion of the earplug to be ablated is identified, the laser is activated so as to direct an emitted laser light toward the portion to be ablated, and the portion to be ablated is removed by ablation. The invention is also directed to an earplug including a body having a feature formed by laser ablation.

The above discussed and other features and advantages of the present invention will be appreciated and understood by those skilled in the art from the following detailed description and drawings.

BRIEF DESCRIPTION OF DRAWINGS

Referring now to the drawings wherein like elements are numbered alike in the several FIGURES.

DETAILED DESCRIPTION OF INVENTION

Figure 1:
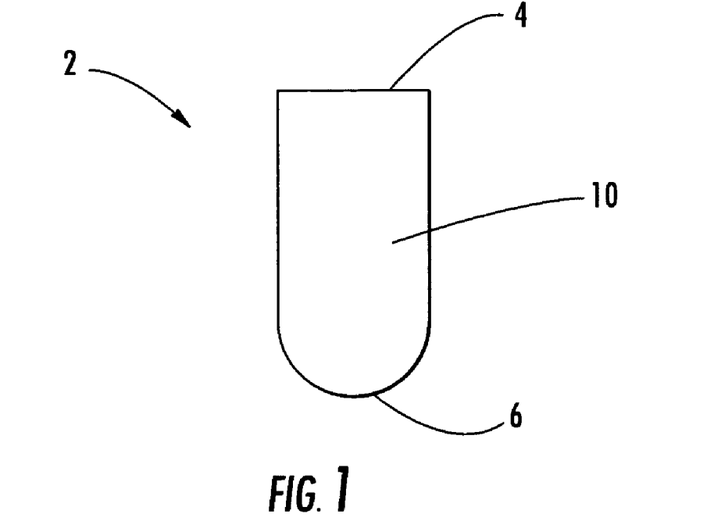
FIG. 1 is an elevational view of an earplug according to the invention.

FIG. 1 shows an earplug 2 according to one embodiment of the invention. The earplug 2 is composed of a compressible, resilient material such as, for example, a foam or rubber material. The earplug 2 generally comprises a body 10 including a first end 4 and an opposite second end 6. During use, a wearer inserts the second end 6 into an ear canal such that the earplug body 10 blocks the ear canal and thus attenuates sound. During insertion, the first end 4 remains at the opening of the ear canal or extends therefrom.

Figure 2:
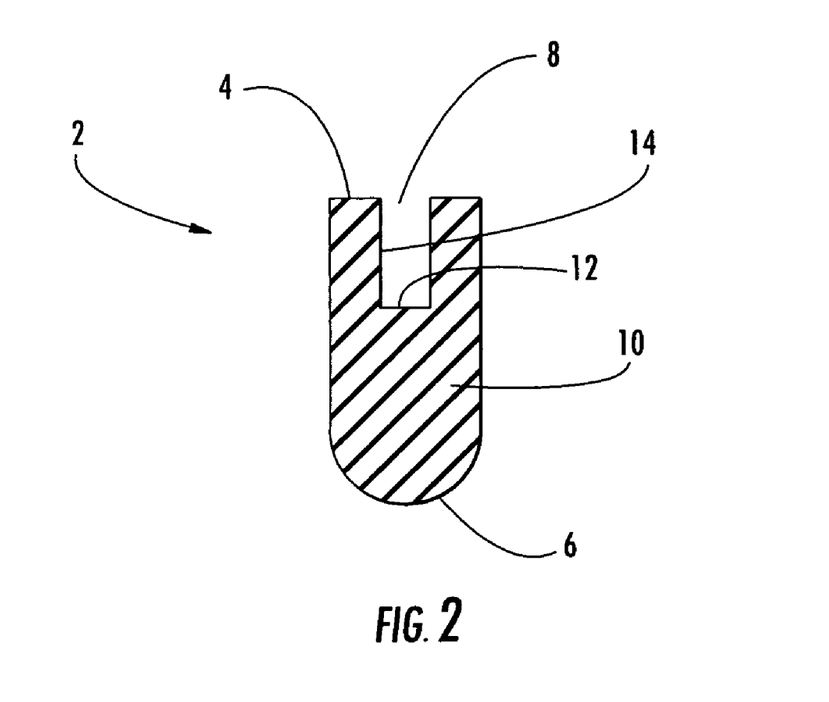
FIG. 2 is a cross-sectional view of the earplug of FIG. 1.

The earplug 2 further comprises, as shown in FIG. 2, a cavity 8 formed in the body 10 of the earplug. As mentioned above, the term "cavity" is used herein to designate a hole or recess formed in the sound attenuating element of an earplug but not completely through the sound attenuating element. In one embodiment, the cavity 8 is essentially a recess set into the earplug 2 and includes a cylindrical cross-section. A bottom portion 12 of the cavity 8 is perpendicular with respect to a longitudinal axis of the cavity while side walls 14 are parallel to the longitudinal axis. Alternatively, of course, the bottom portion 12 and side walls 14 may be spherical, semi-spherical, or angular in shape and disposition.

Figure 3:
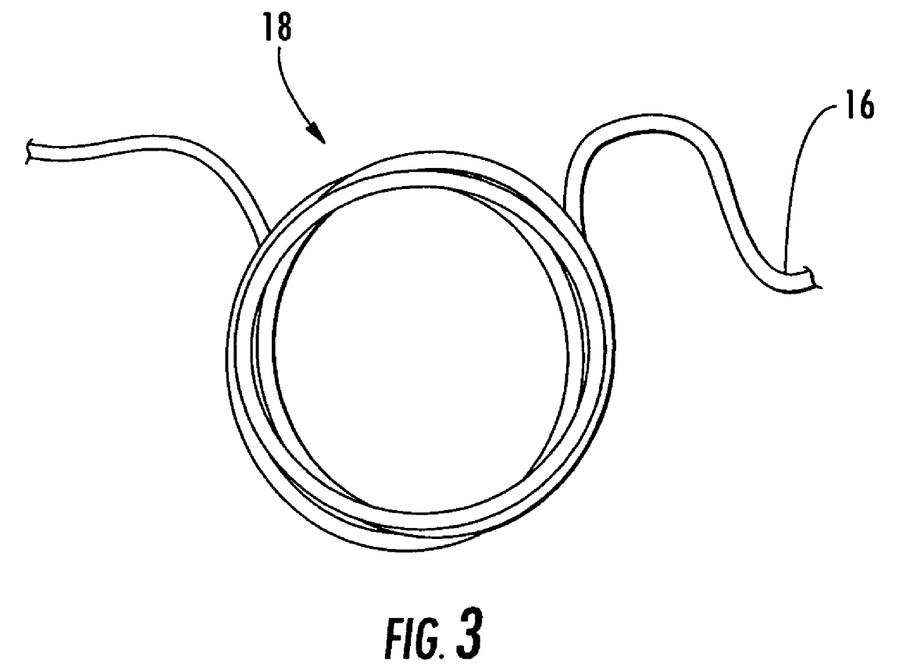
FIG. 3 is an elevational view of a cord.

The cavity 8, in one embodiment, receives an end 16 of a cord 18 (see FIG. 3) which serves to connect the earplug 2 with a second earplug. The end 16 of the cord 18 is inserted into the cavity 8 and bonded therein to the compressible, resilient material of the earplug 2, thus forming a corded pair of earplugs.

For adequate and consistent bonding of the cord 18 and earplug 2 within the cavity 8, it is essential that the cavity 8 is formed in the earplug 2 at a predetermined angle with precise dimensions of depth and width. Also, it is critical that the bottom portion 12 and side walls 14 of the cavity 8 are formed as smooth, consistent mating surfaces in order to facilitate the described bonding.

Referring now to FIGS. 1-4, a method of manufacturing the earplug 2 will now be discussed. First, the earplug body 10 is formed. Any acceptable process may be used to form the earplug body 10 such as, for example, molding, extrusion, casting, etc. In the molding process, the compressible, resilient material, of which the earplug body is formed, is inserted in a liquid form into a mold and allowed to take the shape of the mold. The compressible resilient material is then cured and the earplug body 10, without the cavity 8, is ejected from the mold.

Figure 4:
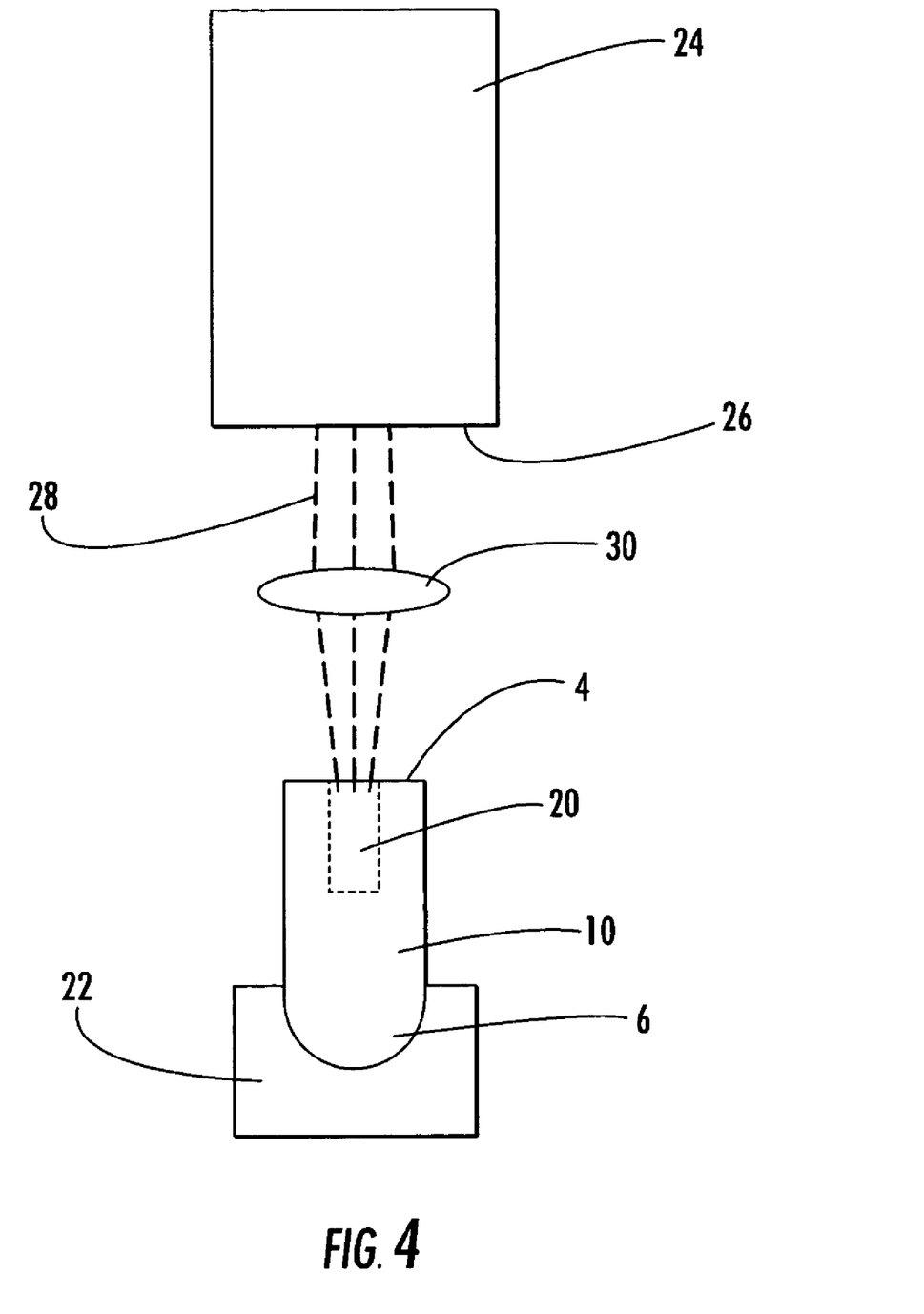
FIG. 4 is a schematic representation of a method of forming the earplug of FIG. 1.

Next, the cavity 8 is formed in the earplug body 10. First, an ablation portion 20 of the compressible, resilient material forming the body 10 is identified for removal. The ablation portion 20 is located at the first end 4 of the body 10 and extends toward the second end 6. The earplug body 10 is disposed in a fixture 22 and positioned proximate a laser 24 such that the ablation portion 20 is facing a laser light emitting end 26 of the laser 24. Laser light 28 is emitted from the light emitting end 24 and propagated toward the earplug body 10. A lens 30 is used to provide a predetermined spot size. The laser light 28 is directed through the lens 30 to the ablation portion 20 so as to completely ablate the portion 20 from the earplug body 10. Once ablation has occurred, propagation of the laser light 28 is terminated and the completed earplug 2, including the newly formed cavity 8, is removed from the fixture 22. The earplug 2 may then be further manufactured, for example, the end 16 of the cord 18 may then be inserted into the cavity 8 and adhesively bonded to the bottom portion 12 and side walls 14 thereof.

The laser 22 used in manufacturing the earplug 2 may be any type of laser suitable for forming the cavity 8 in the earplug body 10 as described. For example, the laser 22 may be any suitable solid-state, gas, excimer, dye, or semiconductor laser.

In one embodiment, a carbon dioxide ($CO_2$) gas laser is used to ablate the earplug body 10 in order to form the cavity 8, where the cavity 8 has a diameter of 0.050". More particularly, a $CO_2$ laser is utilized having an-output power of 25 W, a beam diameter of about 3.5 mm, a beam divergence of about 4 mR, and a wavelength in the range of 10.57-10.63 um. The lens 30, in this embodiment, is a four inch (4") lens which provides a spot size of 0.050". The ablation portion 20 is removed and the cavity 8 is formed with a 250 ms pulse using 5 psi air assist. A suitable $CO_2$ laser is, for example, the "Series 48-2 $CO_2$ Laser" produced commercially by Synrad, Inc.

The cavity 8 formed by laser ablation in the earplug 2 is described, in one embodiment, as having a diameter of 0.050" and as being used to receive an end 16 of a cord 18 to facilitate attachment of the cord 18 to the earplug 2. However, it is of course contemplated within the scope of the invention that the cavity 8 formed in the earplug body may be of different shapes and/or sizes depending on a desired application of a particular earplug.

Figure 5:
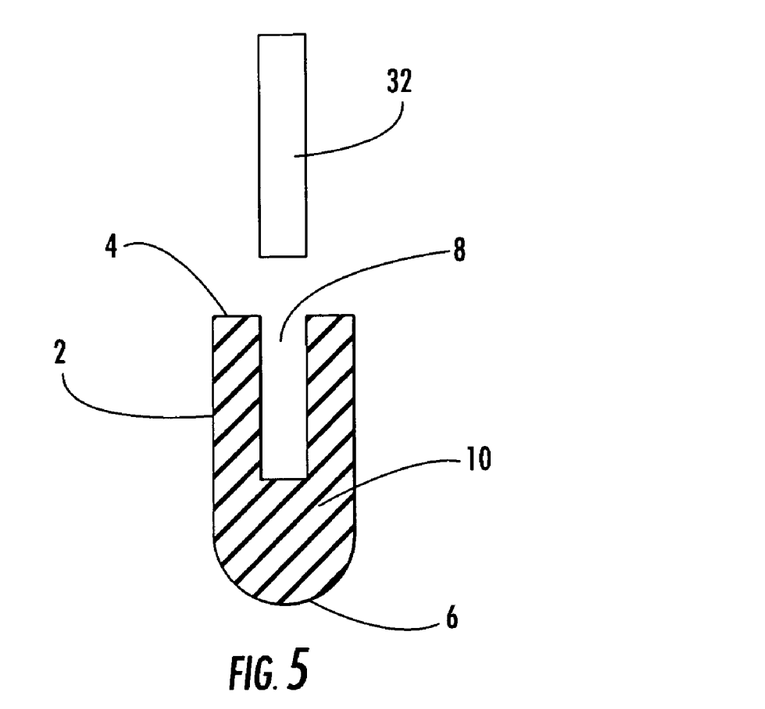
FIG. 5 is a cross-sectional view of the earplug of FIG. 1 in another embodiment.

For example, the cavity 8 may be formed by laser ablation to receive a stem component 32 as shown in FIG. 5. Here, the cavity 8 is given a diameter and shape to enable proper reception and mounting of the stem component 32. The stem component 32 may ultimately be disposed entirely within the body 10 of the earplug 2 or one end of the stem component 32 may be left extending from the first end 4 of the earplug 2. The stem component 32 is composed of a rigid or semi-rigid material in order to impart a degree of rigidity to the earplug 2.

Figure 6:
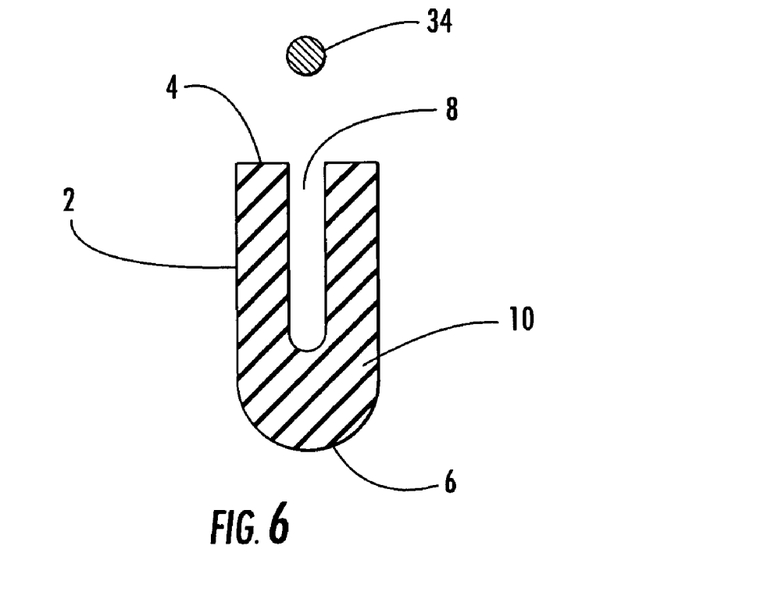
FIG. 6 is a cross-sectional view of the earplug of FIG. 1 in another embodiment.

In another example, the cavity 8 may be formed by laser ablation, as described, to receive a detectable insert 34 as shown in FIG. 6. The detectable insert 34 is composed of any readily detectable material, such as, for example a material which is metal, magnetic, or x-ray detectable. The detectable insert 34 is preferably spherical in shape and may be used in combination with the cord 18 previously described to form a corded pair of detectable earplugs.

In still another example, the cavity 8 may be formed by laser ablation, as described, to produce a reduced pressure zone within the earplug body 10 proximate the cavity 8. When the earplug 2 is inserted into the ear canal, the body 10 is compressed and then allowed to expand within the canal. The pressure exerted outwardly during expansion of the earplug body 10 is less at the reduced pressure zone then at other portions of the earplug. The reduced expansion pressure of the reduced pressure zone, formed by laser ablation, enhances comfort to the wearer.

Figure 7A:
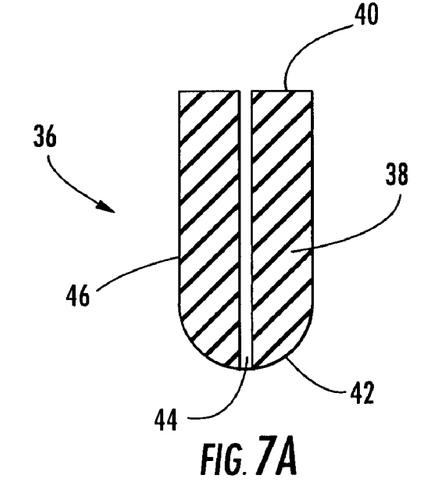
FIGS. 7A-7C are cross-sectional views of earplugs according to the invention.

FIG. 7A shows an earplug, in another embodiment of the invention, generally designated by reference numeral 36. Earplug 36 includes a body 38 having first and second opposite ends 40 and 42, respectively. The first and second ends 40 and 42 are generally analogous to first and second ends 4 and 6, respectively, discussed above. The earplug 36 further includes a channel 44 formed through the earplug body 38 from the first end 40 to the second end 42. As discussed above, the term "channel" will be used herein to designate a hole or recess formed in a sound attenuating element of an earplug which propagates completely through the sound attenuating element such that the channel is open to an exterior of the earplug in at least two places. As such, the channel 44 is a narrow passageway which traverses the length of the earplug 36 and includes an opening at the first end 40 and an opening at the second end 42. Similar to the earplug 2, the earplug 36 is composed of a compressible, resilient material such as, for example, a foam material or a rubber material.

The channel 36 may be used to facilitate sound propagation. For example, in one embodiment, the channel 36 is utilized to permit the passage of certain sounds from the first end 40, through the earplug body 38, to the second end 42 which, during use, is disposed proximate the eardrum of the wearer. The channel 44 is shown in the Figures as extending from the first end 40 to the second end 42 in a path generally parallel to a longitudinal axis of the earplug 36. However, in another embodiment, the channel 44 may be formed to traverse the earplug body 38 from a side portion 46 to the second end 42. Still further, the earplug 36 as shown may include one or more addition channels extending from the side portion 46 to the first end 40. In this way, various sound propagation pathways are possible.

Figure 7B:
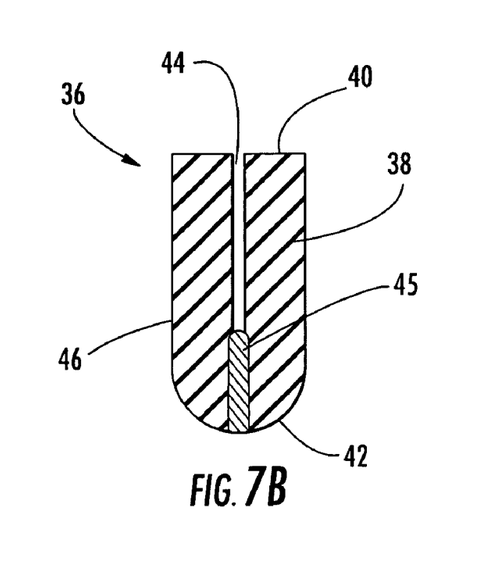
Figure 7C:
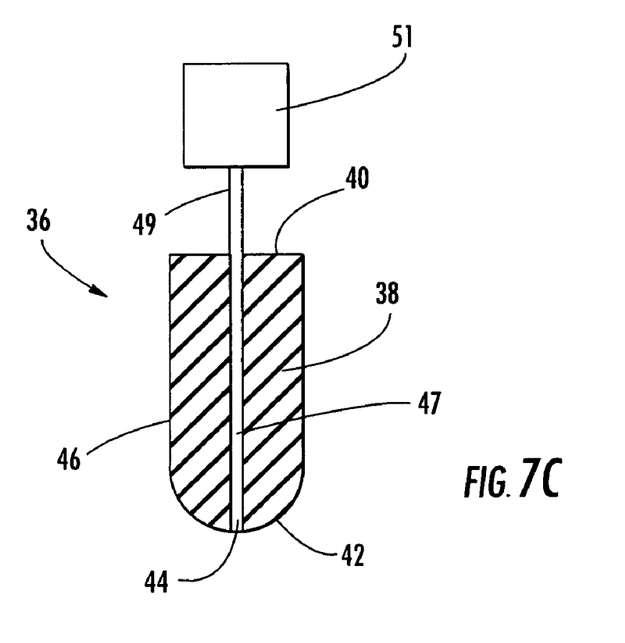

In another embodiment, the channel 44 receives equipment to facilitate communications. For example, as shown in FIG. 7B, the channel may receive a communication insert 45 such as a receiver or a transducer which then may be bonded or otherwise retained within the earplug body 38 and utilized to deliver sound to the ear canal of a wearer. Alternatively, the channel 44 may receive a tube element 47, as shown in FIG. 7C. The tube element 47 is a hollow member which maintains a passageway in the earplug body 38 through which sounds may be propagated. An end 49 of the tube element 47 extends from the channel 44 to an exterior of the earplug 36. The tube element 47 may be connected to a communication assembly 51 at the end 49. The communication assembly 51 produces sounds which are propagated through the passageway of the tube element 47 to the ear canal of a wearer.

Referring now to FIGS. 7A-7C and 8, a method of manufacturing the earplug 36 will now be discussed. First, the earplug body 38 is formed, without the channel 44, through any conventional process including, for example, molding, extrusion, casting, etc. In such a molding process, the resilient, compressible material, in pliable form, is poured into a mold wherein the material cures and thus forms the earplug body 38, absent the channel 44.

Figure 8:
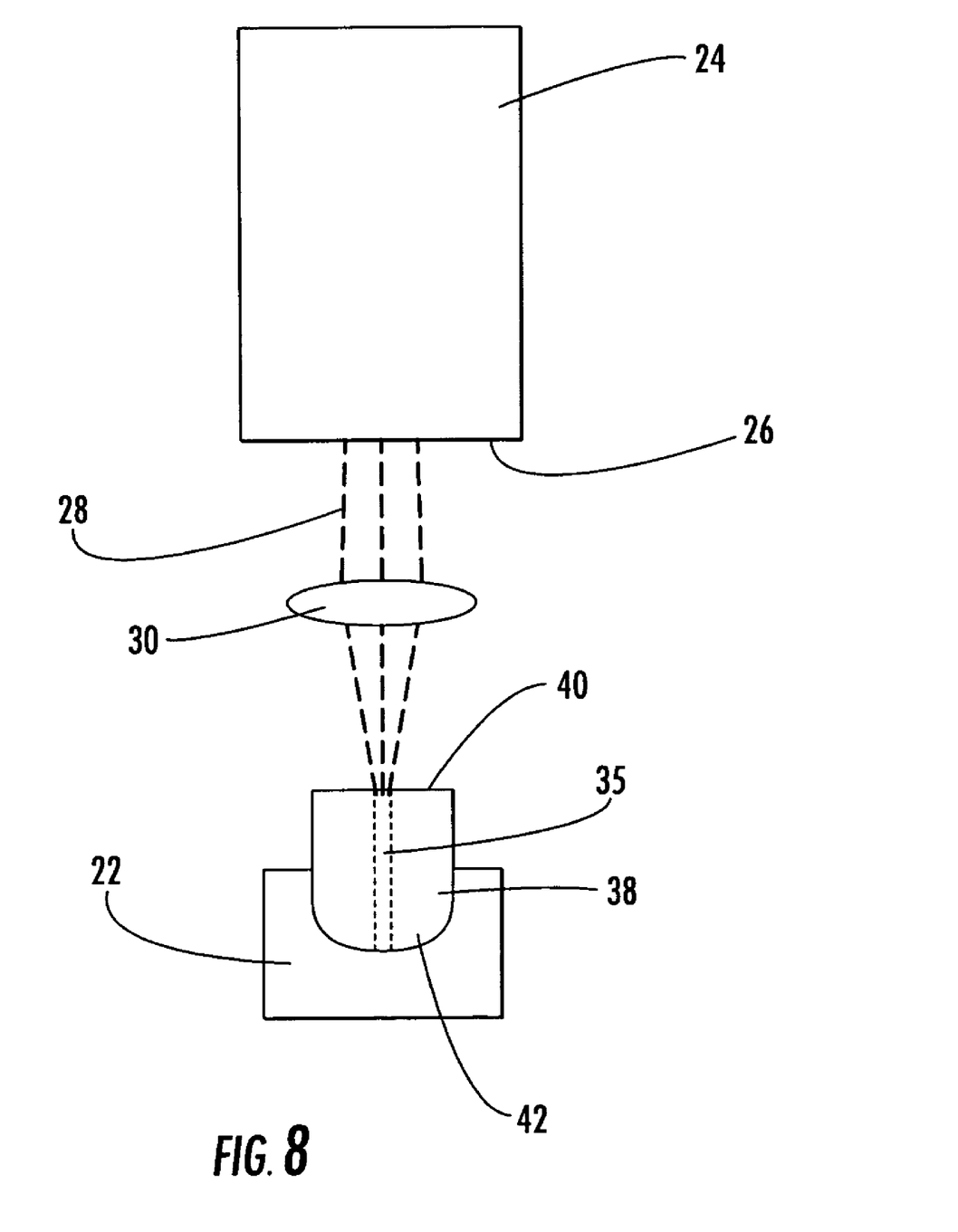
FIG. 8 is a schematic representation of a method of forming the earplugs of FIGS. 7A-7C.

The formed earplug body 38 is then removed from the mold and placed in the fixture 22 wherein the earplug body 38 is compressed to a reduced height. An ablation portion 35 of the earplug body 38 is identified which corresponds to the compressible, resilient material which must be removed to form the channel 44. The earplug body 10 is positioned proximate the laser 24 such that the ablation portion is disposed adjacent the laser light emitting end 26. The laser 24 is activated to emit laser light 28 from end 26 through the lens 30 which provides a predetermined spot size. The laser light 28 is directed through the lens 30 to the ablation portion 35 so as to completely remove the ablation portion 35 of the earplug body 38 and, thus, form the channel 44.

Once ablation has occurred, the laser light 28 is terminated and the completed earplug 36, including the newly formed channel 44, is removed from the fixture 22. The earplug 36 may then be further manufactured, for example, the communication insert 45 or the tube element 47 may be inserted in the channel 44 and bonded therein to the earplug body 38.

Any suitable laser may be used for ablation purposes in forming the channel 44 including, but not limited to, solid-state, gas, excimer, dye, or semiconductor lasers.

In one embodiment, a carbon dioxide ($CO_2$) gas laser is used to ablate the earplug body 10 in order to form the channel 44, where the channel 44 has a diameter of 0.090". The $CO_2$ laser, similar to that described above with reference to the earplug 2, includes an output power of 25 W, a beam diameter of about 3.5 mm, a beam divergence of about 4 mR, and a wavelength in the range of 10.57-10.63 um. The lens 30, in this embodiment, is a four inch (4") lens with a 7.5" focal length which provides a spot size of 0.090". The speed of the laser is set at 20 inches per minute and 40 psi of air assist is utilized The "Series 48-2 $CO_2$ Laser" produced commercially by Synrad, Inc., may be used to form the channel 44.

As mentioned, the earplug body 38 is compressed in the fixture 22 prior to ablation. Preferably, in the example described, the body 38 is compressed to a height of 0.15". Such compression enables accurate and consistent removal of the ablation portion 35, thus facilitating formation of the channel 44.

Figure 9:
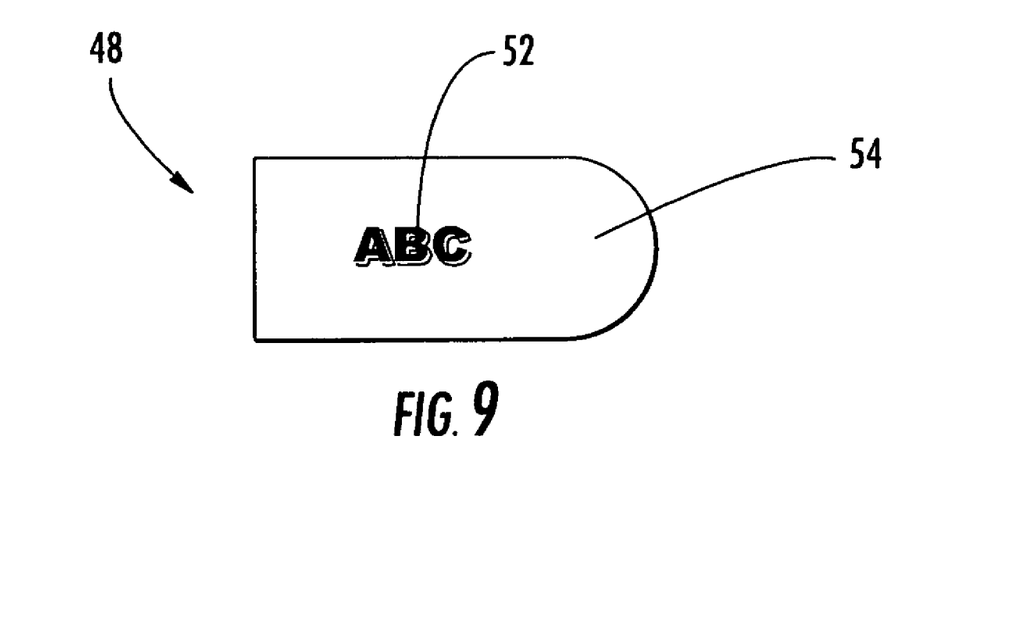
FIG. 9 is an elevational view of an earplug according to the invention.
Figure 10:
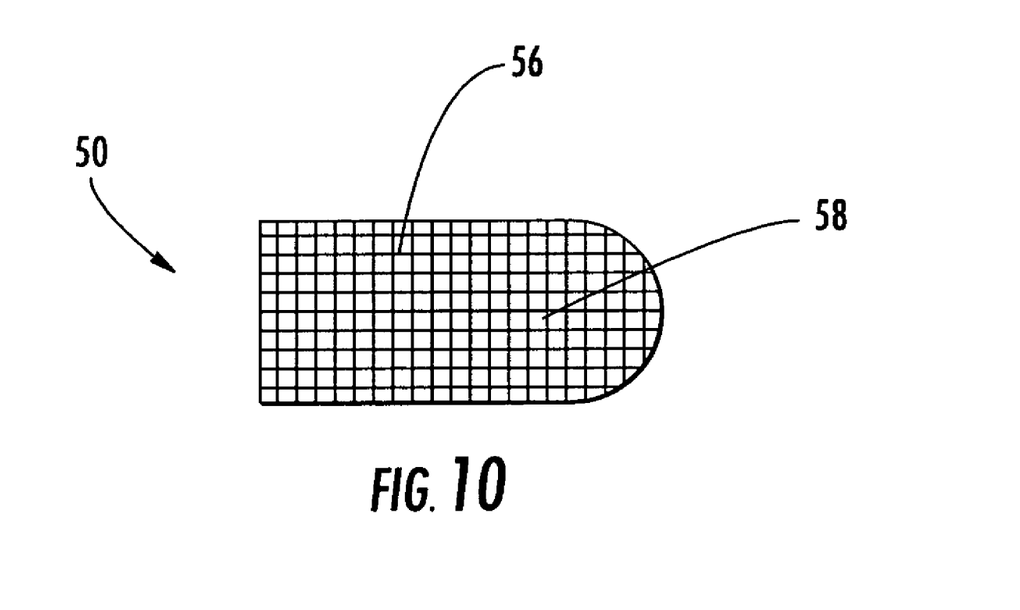
FIG. 10 is an elevational view of an earplug according to the invention.

In another embodiment of the invention, earplugs 48 and 50 are formed as shown in FIGS. 9 and 10, respectively. Earplug 48 includes indicia 52 formed on an outer surface 54. Earplug 50 includes a pattern 56 formed on an outer surface 58. Both the indicia 52 and the pattern 56 are essentially scored into the respective outer surfaces, 54 and 58.

The scoring of the indicia 52 and of the pattern 56 is performed by laser ablation as follows. First, the earplugs 48 and 50, not including the indicia 52 or pattern 56, are manufactured through a convention process including, for example, by molding, extrusion, casting, etc. That is, the earplugs 48 and 50 are formed to include smooth and uniform outer surfaces 54 and 58, respectively. Then the earplugs 48 and 50 are each separately placed into the fixture 22 and are subject to laser ablation by the laser 24.

Particularly, with respect to the earplug 48, an ablation portion corresponding to the desired indicia 52 is identified, the earplug 48 is brought proximate the laser 24, and subjected to laser light 28 emitted therefrom. The emitted laser light 28 ablates the ablation portion, thus forming the indicia 52.

A similar technique is used to form the pattern 56 in earplug 50. That is, the earplug 50 is formed having a smooth and uniform outer surface 58 and brought proximate the laser 24. An ablation portion of the outer surface 58 is identified which corresponds to the desired pattern 56. The outer surface 58 is subjected to laser light 28 emitted from the laser 24 incident upon the outer surface 58, thus resulting in the complete ablation of the ablation portion and causing the formation of the pattern 56.

The indicia 52 and pattern 56 are only described and shown herein generally. The indicia 52 includes any letters, characters, etc. and may be designed to represent, for example, brand or trade names. The pattern 56 is limited only by the accuracy of the chosen laser and may generally comprise any arrangement of ablated characters, lines, shapes, etc. which may be represented singularly or in combination as surface ornamentation on the earplug 50.

Any suitable laser may be used for ablation purposes in forming the indicia 52 and pattern 56 including, but not limited to, solid-state, gas, excimer, dye, or semiconductor lasers. In a preferable embodiment, a $CO_2$ gas laser as made commercially available by Synrad, Inc., may be used.

Figure 11A:
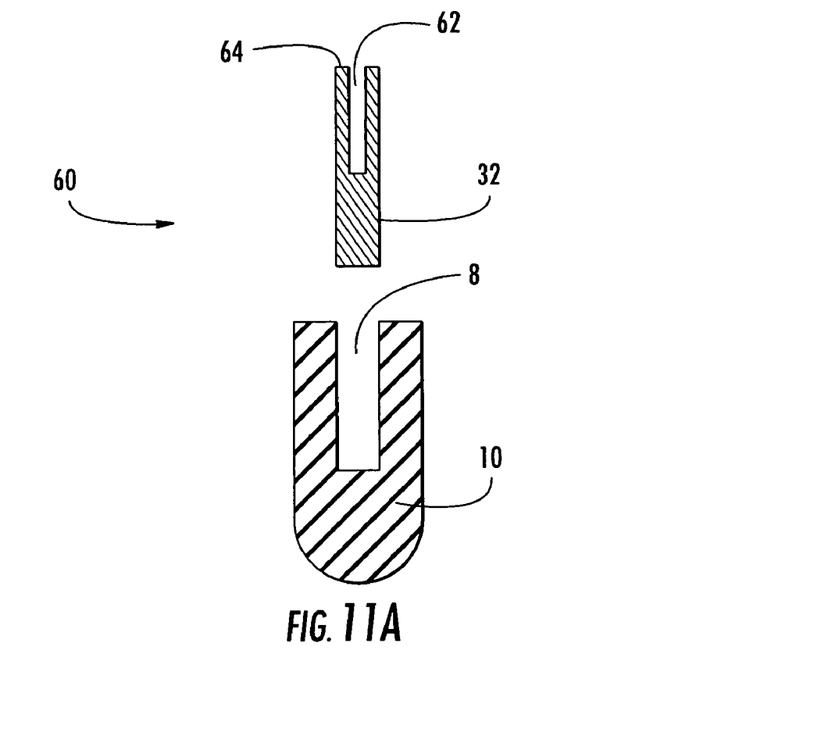
FIGS. 11A-B are cross-sectional views of earplugs according to the invention.

FIG. 11A shows an earplug 60 in another embodiment of the invention. Earplug 60 includes the stem component 32, the cavity 8, and the earplug body 10 as shown in FIG. 5. However, the earplug 60 also includes a stem cavity 62 formed in a first end 64 of the stem component 32.

The stem cavity 62 may generally be formed to have any desired dimension or disposition. In one embodiment, the stem cavity 62 is cylindrical in shape and extends into the stem 32 along a longitudinal axis of the stem 32. The cavity 62 may be used to receive the end 16 of the cord 18 shown in FIG. 3. The cord 18 may then be correspondingly bonded to the stem component 32 in the stem cavity 62. Thus, a corded, stemmed, pair of earplugs is produced.

Of course, the stem cavity 62 could be used to receive other items such as, for example, the detectable insert 34 shown if FIG. 6. As described, the detectable insert 34 is composed of any readily detectable material such as, for example, a material which is metal, magnetic, or x-ray detectable. Accordingly, a stemmed, detectable earplug may be formed according to the invention.

The stem cavity 62 is formed through laser ablation. First, the stem component 32 is formed through, for example, a molding or extruding process. Then the stem component 32 is brought proximate the laser 24 described and shown herein. Laser light 28 is emitted from the laser 24 and directed incident to the stem component 32. A portion of the stem component 32 which corresponds to the stem cavity is subjected to the laser light 28 and subsequently ablated, thus forming the stem cavity 62. It is noted that the stem cavity 62 may be formed in the stem component 32 before or after the stem component is fixed to the earplug body 10.

The stem component 32, as mentioned, is a rigid or semi-rigid element and may be composed of any suitable plastic or rubber type material. Further, the stem component 32 may be composed of a porous material.

Formation of a cavity within a stem of an earplug by laser ablation has been discussed above. The scope of the invention, however, includes any application of laser ablation to the earplug stem. For example, laser ablation may be used to form surface ornamentation, such as indicia or patterning, in the stem. Further, laser ablation may be utilized to shape or contour the stem as desired, or to form a channel entirely through the stem, or to form any other surface feature in the stem.

Figure 11B:
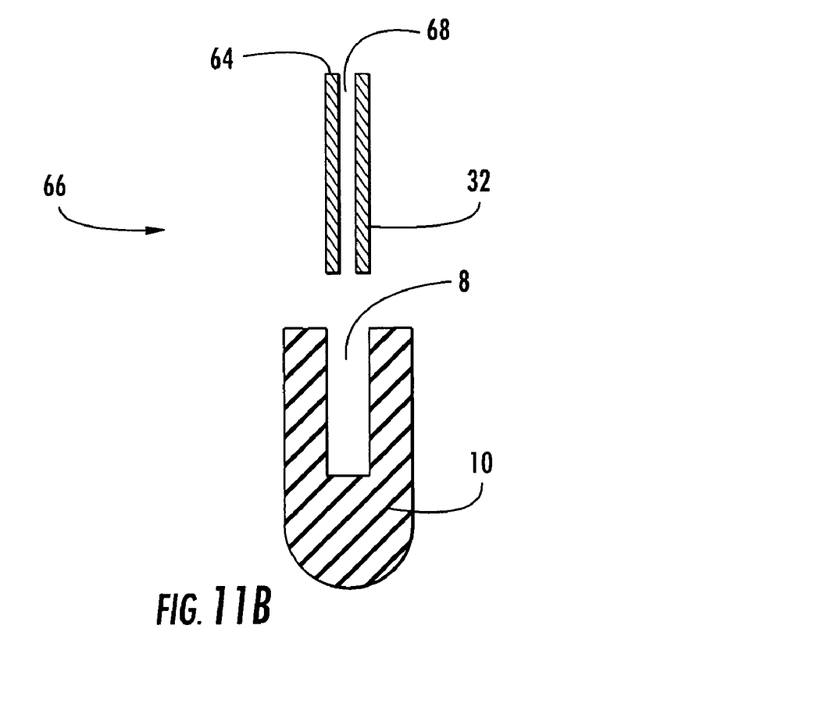

For example, FIG. 11A shows an earplug 66 including the body 10 having the cavity 8 formed therein for receiving the stem 32. The stem 32 includes a channel 68 formed entirely through the stem 32. The channel 68 is formed by laser ablation as discussed herein and may be used to receive and retain therein, for example, the communication insert 45 or the tube element 47 of FIGS. 7B and 7C, respectively, to thus facilitate communications with a wearer.

The invention, as described and contemplated herein, provides an effective, efficient, and consistent method for removing material from an earplug to form surface elements in the earplug, such as a cavity, a through-channel, and surface ornamentation.

While preferred embodiments have been shown and described, various modifications and substitutions may be made thereto without departing from the spirit and scope of the invention. Accordingly, it is to be understood that the present invention has been described by way of illustrations and not limitation.

The invention claimed is:

1. A method of forming an earplug, comprising:
   removing a material by laser ablation;

wherein said removing the material comprises forming a cavity in the earplug;

wherein said removing the material further comprises forming the cavity in a first end of a sound attenuating portion of the earplug, the cavity having a cylindrical shape and extending into the sound attenuating portion, along a longitudinal axis of the sound attenuating portion, toward a second end of the sound attenuating portion opposite the first end;

where the method further comprises inserting and retaining at least one of a cord, a stem, and a detectable insert in the cavity.

2. A method of forming an earplug, comprising:

removing a material by laser ablation;

wherein said removing the material comprises forming a cavity in the earplug;

wherein said removing the material further comprises forming the cavity in a first end of a stem portion of the earplug, the cavity having a cylindrical shape and extending into a body of the stem, along a longitudinal axis of the stem, toward a second end of the stem opposite the first end, the earplug including a sound attenuating element attached to the stem at the second end.

3. The method of claim 2, further comprising inserting and retaining at least one of a cord and a detectable insert in the cavity.

4. A method of forming an earplug, comprising:

removing a material by laser ablation;

wherein said removing the material comprises forming a channel through at least a portion of the earplug;

wherein said removing the material further comprises forming the channel in a stem portion of the earplug, the channel having a first opening at a first end of the stem and a second opening at a second end of the stem opposite the first end, the channel traversing a longitudinal length of the stem from the first opening to the second opening, the earplug including a sound attenuating element attached to the stem at the second end.

5. A method of forming an earplug, comprising:

positioning the earplug proximate a laser;

identifying a portion of the earplug to be ablated;

activating the laser so as to direct an emitted laser light toward the portion to be ablated; and ablating the portion to be ablated;

wherein the portion to be ablated comprises a portion of the earplug corresponding to a channel to be formed through at least a portion of the earplug, and wherein said ablating the portion forms the channel;

wherein said channel is formed in a sound attenuating portion of the earplug and said positioning the earplug comprises disposing the sound attenuating portion in a fixture, compressing the sound attenuating portion in the fixture, maintaining the sound attenuating portion under compression, and positioning the fixture proximate the laser.

6. A method of forming an earplug, comprising:

positioning the earplug proximate a laser;

identifying a portion of the earplug to be ablated;

activating the laser so as to direct an emitted laser light toward the portion to be ablated; and ablating the portion to be ablated;

wherein the portion to be ablated comprises a portion of the earplug corresponding to a cavity to be formed in the earplug, and wherein said ablating the portion forms the cavity; the method further comprising receiving and retaining at least one of a cord, a stem component, and a detectable insert in the cavity.

* * * * *